US006947128B2

(12) United States Patent
Basiji et al.

(10) Patent No.: US 6,947,128 B2
(45) Date of Patent: Sep. 20, 2005

(54) ALTERNATIVE DETECTOR CONFIGURATION AND MODE OF OPERATION OF A TIME DELAY INTEGRATION PARTICLE ANALYZER

(75) Inventors: David A. Basiji, Seattle, WA (US); William E. Ortyn, Bainbridge Island, WA (US)

(73) Assignee: Amnis Corporation, Seattle, WA (US)

( * ) Notice: Subject to any disclaimer, the term of this patent is extended or adjusted under 35 U.S.C. 154(b) by 0 days.

(21) Appl. No.: 10/602,252

(22) Filed: Jun. 23, 2003

(65) Prior Publication Data
US 2004/0085527 A1 May 6, 2004

Related U.S. Application Data

(63) Continuation of application No. 09/932,844, filed on Aug. 17, 2001, now Pat. No. 6,583,865.
(60) Provisional application No. 60/228,078, filed on Aug. 25, 2000.

(51) Int. Cl.[7] .................................................. G01J 3/14
(52) U.S. Cl. ....................................................... 356/73
(58) Field of Search .......................... 356/73, 319, 326, 356/328, 317, 318, 305; 250/226

(56) References Cited

U.S. PATENT DOCUMENTS

| 3,922,069 A | 11/1975 | Kishikawa et al. ......... 359/633 |
| 4,770,992 A | 9/1988 | Van den Engh et al. ........ 435/6 |
| 4,786,165 A | 11/1988 | Yamamoto et al. ............ 356/23 |
| 5,096,807 A | 3/1992 | Leaback ......................... 435/6 |
| 5,141,609 A | 8/1992 | Sweedler et al. ........... 356/344 |
| 5,159,397 A | 10/1992 | Kosaka et al. ................. 356/73 |

(Continued)

FOREIGN PATENT DOCUMENTS

| WO | WO 00/42412 | 7/2000 | .......... G01N/15/02 |

OTHER PUBLICATIONS

Kubota, Fumio et al. 1995. "Flow Cytometer and Imaging Device Used in Combination." *Cytometry*: 21:129–132.

Kubota, F. 2003. "Analysis of red cell and platelet morphology using an imaging–combined flow cytometer." *Clin. Lab. Haem.*: 25:71–76.

Ong, S.H. and P.M. Nikolls. 1991. "Optical Design in a Flow System For Imagina Cells." *Sciences in Medicine*: 14:2:74–80.

Ong, S.H. and P.M. Nickolls. 1994. "Analysis of MTF Degradation in the Imaging of Cells in a Flow System." *International Journal of Imaging Systems & Technology*: 5:243–250.

Satoh, Kaneo et al. 2002. "Small Aggregates of Platelets Can Be Detected Sensitively by a Flow Cytometer Equipped With an Imaging Device: Mechanisms of Epinephrine–Induced Aggregation and Antiplatelet Effects of Beraprost." *Cytometry*: 48:194–201.

(Continued)

*Primary Examiner*—Michael P. Stafira
(74) *Attorney, Agent, or Firm*—Ronald M. Anderson

(57) ABSTRACT

Light from an object moving through an imaging system is collected, dispersed, and imaged onto a time delay integration (TDI) detector that is inclined relative to an axis of motion of the object, producing a pixilated output signal. In one embodiment, the movement of the image object over the TDI detector is asynchronous with the movement of the output signal producing an output signal that is a composite of the image of the object at varying focal point along the focal plane. In another embodiment, light from the object is periodically incident on the inclined TDI detector, producing a plurality of spaced apart images and corresponding output signals that propagate across the TDI detector. The inclined plane enables images of FISH probes or other components within an object to be produced at different focal points, so that the 3D spatial relationship between the FISH probes or components can be resolved.

10 Claims, 6 Drawing Sheets

U.S. PATENT DOCUMENTS

| | | | |
|---|---|---|---|
| 5,159,398 A | 10/1992 | Maekawa et al. | 356/73 |
| 5,159,642 A | 10/1992 | Kosaka | 382/6 |
| 5,247,339 A | 9/1993 | Ogino | 356/73 |
| 5,272,354 A | 12/1993 | Kosaka | 250/574 |
| 5,422,712 A | 6/1995 | Ogino | 356/73 |
| 5,444,527 A | 8/1995 | Kosaka | 356/73 |
| 5,453,784 A | 9/1995 | Krishnan et al. | 348/348 |
| 5,471,294 A | 11/1995 | Ogino | 356/73 |
| 5,548,395 A | 8/1996 | Kosaka | 356/73 |
| 5,596,401 A | 1/1997 | Kusuzawa | 356/23 |
| 5,633,503 A | 5/1997 | Kosaka | 250/458.1 |
| 5,644,388 A | 7/1997 | Maekawa et al. | 356/73 |
| 5,674,743 A | 10/1997 | Ulmer | 435/287.2 |
| 5,695,934 A | 12/1997 | Brenner | 435/6 |
| 5,754,291 A | 5/1998 | Kain | 356/338 |
| 5,760,899 A * | 6/1998 | Eismann | 356/326 |
| RE35,868 E | 8/1998 | Kosaka | 250/574 |
| 5,831,723 A | 11/1998 | Kubota et al. | 356/73 |
| 5,848,123 A | 12/1998 | Strommer | 378/98.8 |
| 5,855,753 A | 1/1999 | Trau et al. | 204/484 |
| 5,929,986 A | 7/1999 | Slater et al. | 356/326 |
| 5,959,953 A | 9/1999 | Alon | 369/44.41 |
| 6,007,994 A | 12/1999 | Ward et al. | 435/6 |
| 6,014,468 A | 1/2000 | McCarthy et al. | 382/254 |
| 6,066,459 A | 5/2000 | Garini et al. | 435/6 |
| 6,072,529 A | 6/2000 | Mutze | 348/351 |
| 6,116,739 A | 9/2000 | Ishihara et al. | 353/31 |
| 6,156,465 A | 12/2000 | Cao et al. | 430/30 |
| 6,210,973 B1 | 4/2001 | Pettit | 436/172 |
| 6,211,955 B1 | 4/2001 | Basiji et al. | 356/326 |
| 6,249,341 B1 | 6/2001 | Basiji et al. | 356/73 |
| 6,256,096 B1 | 7/2001 | Johnson | 356/335 |
| 6,330,081 B1 | 12/2001 | Scholten | 358/463 |
| 6,381,363 B1 | 4/2002 | Murching et al. | 382/164 |
| 6,522,781 B1 | 2/2003 | Norikane et al. | 382/203 |
| 6,583,865 B2 * | 6/2003 | Basiji et al. | 356/73 |
| 2001/0006416 A1 | 7/2001 | Johnson | 356/73 |
| 2002/0126275 A1 | 9/2002 | Johnson | 356/317 |

OTHER PUBLICATIONS

Wang, Fu–sheng and Fumio Kubota. 2002. "A Novel Apoptosis Research Method With Imaging–Combined Flow Cytometer and HITC OR IR–125 Staining." *Cytometry*: 50:267–274.

Wietzorrek, Joachim et al. 1999. "A New Multiparameter Flow Cytometer: Optical and Electrical Cell Analysis in Combination With Video Microscopy in Flow." *Cytometry*: 35:291–301.

Ong, S.–H.; D. Home; C.–K. Yeung, P. Nickolls, T. Cole. "Development of an Image Flow Cytometer." Analytical and Quantitative Cytology and Histology. XIVth International Conference on Medical and Biololgical Engineering and the VIIth International Conference on Medical Physics, Espoo, Finland. Aug. 11–15, 1985: pp 375–382.

Ong, Sim Heng. "Development of a System for Imaging and Classifying Biological Cells in a Flow Cytometer." Doctor of Philosophy Thesis. University of Sydney, School of Electrical Engineering. Aug. 1985.

* cited by examiner

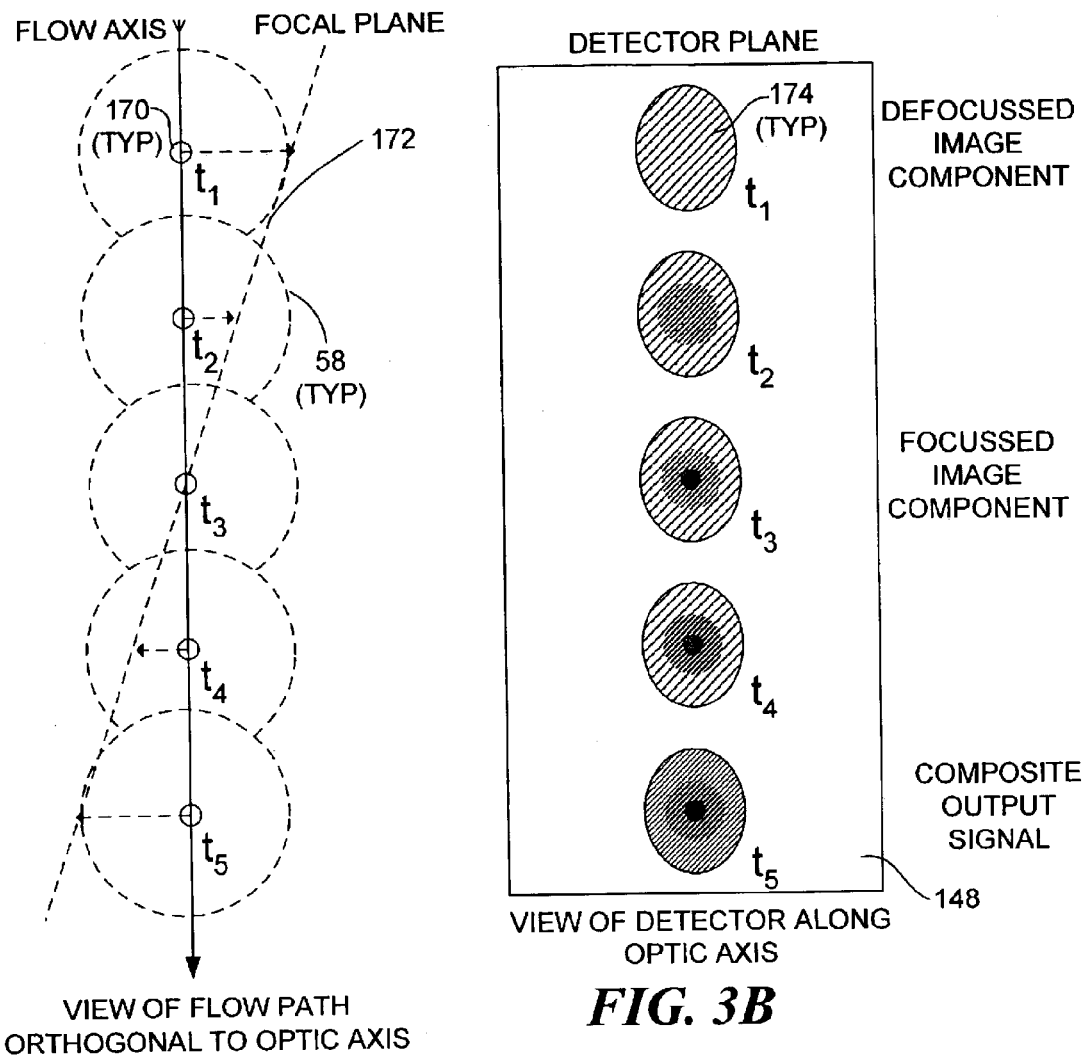
FIG. 3A VIEW OF FLOW PATH ORTHOGONAL TO OPTIC AXIS
FIG. 3B VIEW OF DETECTOR ALONG OPTIC AXIS
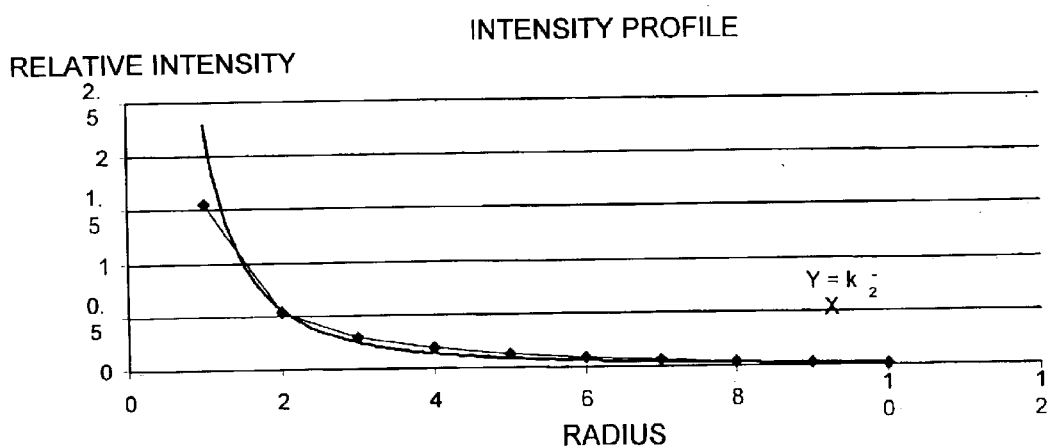
FIG. 3C

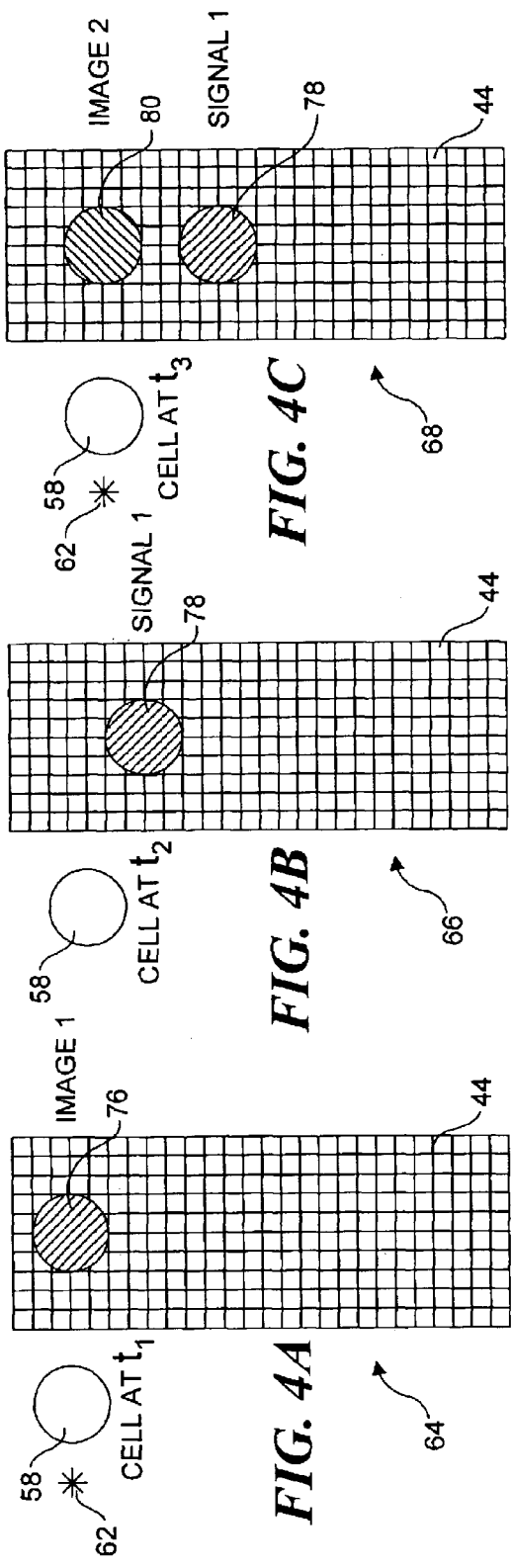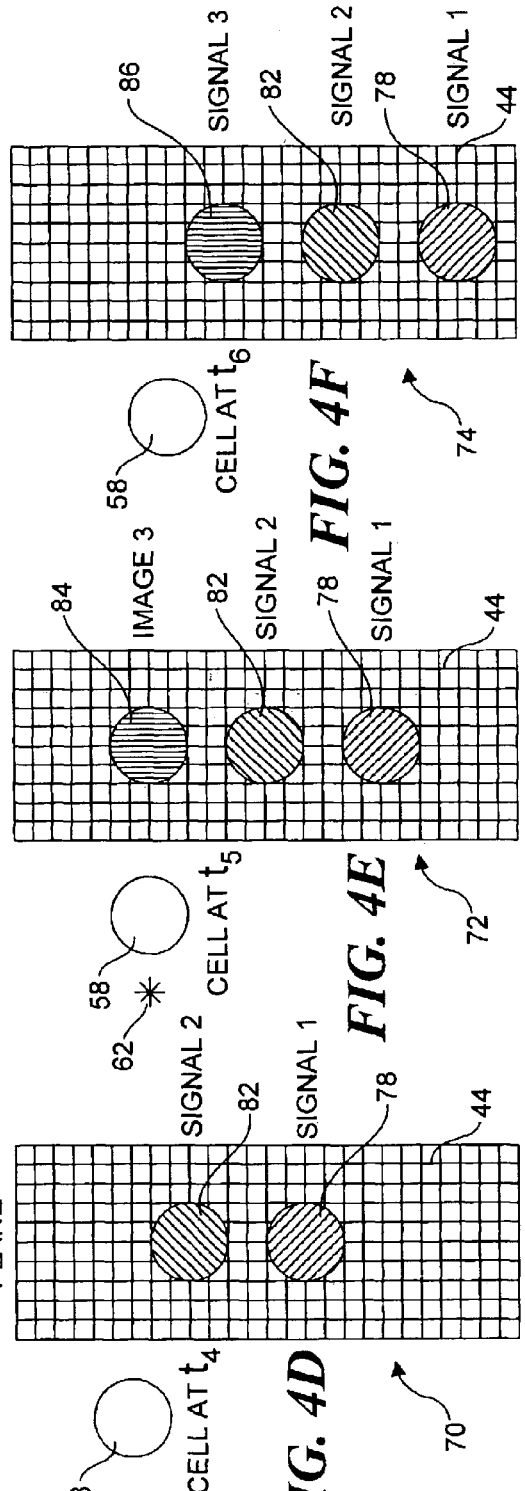

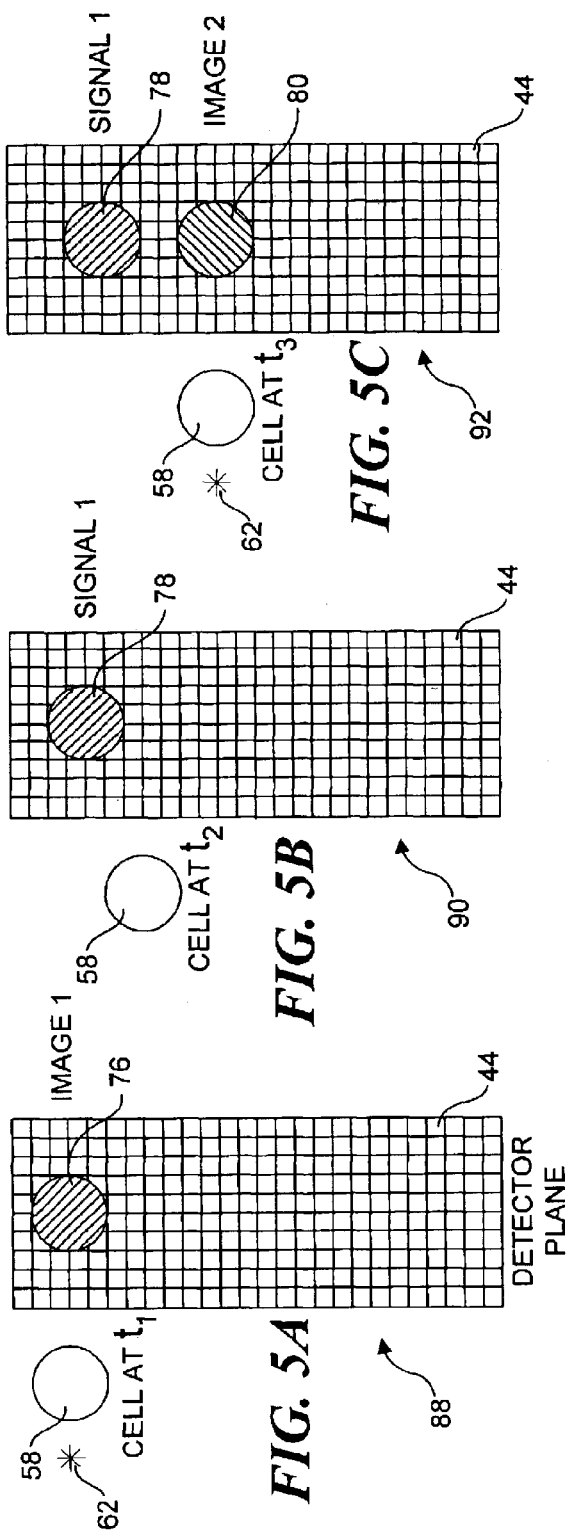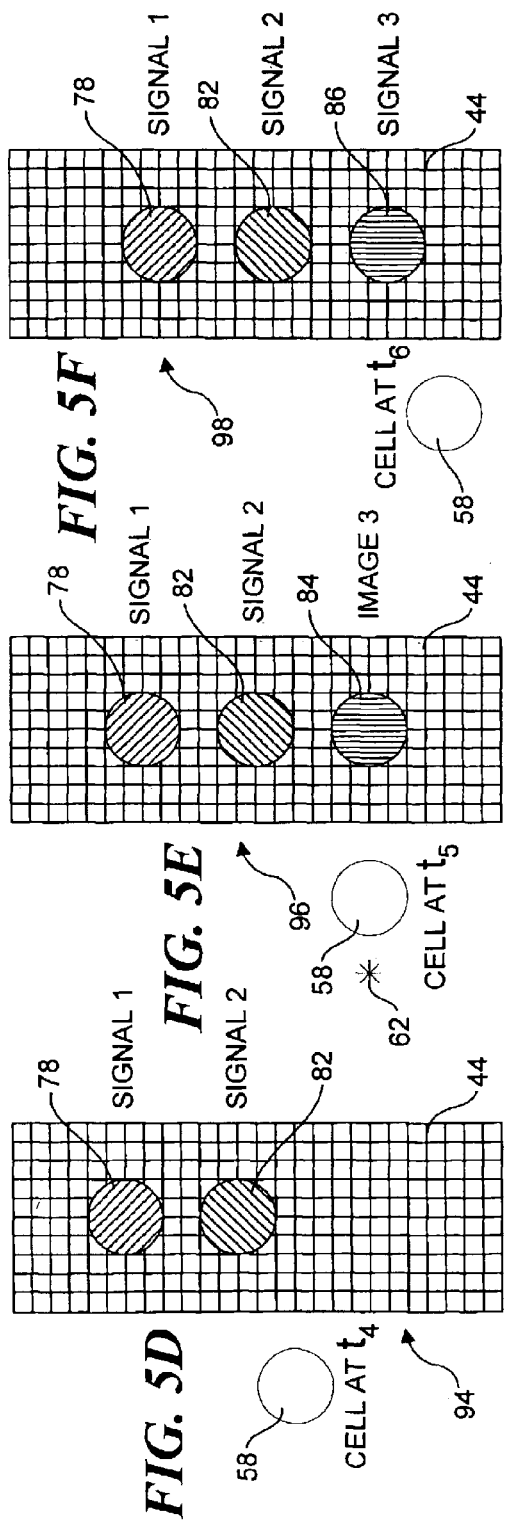

VIEW OF FLOW PATH
ORTHOGONAL TO OPTIC AXIS

IMAGES ACQUIRED AT TIMES
NOTED

ALTERNATIVE DETECTOR CONFIGURATION AND MODE OF OPERATION OF A TIME DELAY INTEGRATION PARTICLE ANALYZER

RELATED APPLICATIONS

This application is a continuation of a patent application Ser. No. 09/932,844, filed on Aug. 17, 2001, now U.S. Pat. No. 6,583,865, which is based on a prior co-pending provisional application Ser. No. 60/228,078, filed on Aug. 25, 2000, the benefits of the filing dates of which are hereby claimed under 35 U.S.C. § 119(e) and 35 U.S.C. § 120.

FIELD OF THE INVENTION

This invention generally relates to imaging objects or particles for purposes of detection and analysis, and more specifically, to a system and method for analyzing the three dimensional structure, contents, and spectral composition of objects, such as cells, which may be in motion.

BACKGROUND OF THE INVENTION

There are a number of biological and medical procedures that are currently impractical due to limitations in cell and particle analysis technology. Examples of such procedures include battlefield detection and monitoring of both known and unknown toxins, non-invasive prenatal genetic testing and routine cancer screening via the detection and analysis of rare cells (i.e., cells having a low rate of occurrence) in peripheral blood, and drug discovery via high throughput cell assays.

New medical and biological procedures increasingly require more advanced cell analysis capabilities than currently exist. One example is the analysis of changes in the genetic constitution of tumor cells for the optimization of chemotherapy. Tumor cells may exhibit unusual DNA changes, such as a variation in the number of chromosomes, the amplification of chemotherapy-resistance genes, or changes in the regulation of gene expression. These changes can be detected using Fluorescence In-Situ Hybridization (FISH) probes that bind to specific DNA sequences within cells. FISH analysis requires an accurate determination of the number of distinct FISH locations within the nucleus of a cell, ideally in three dimensions. Commonly assigned U.S. patent application Ser. No. 09/490,478 describes the use of a stereoscopic imaging apparatus to view fluid-suspended cells from multiple angles, with a high numerical aperture for the accurate enumeration of FISH spots within a cell. This technique can be applied to a slide-mounted sample or a sample on a micro-fluidic chip, but generally with lower numerical apertures, due to the difficulty of coupling orthogonal collection systems to the flat sample substrate. Clearly, it would be preferable to perform three-dimensional (3D) imaging of cells on slides or in micro-capillaries with a single collection system in order to enable light collection with a high numerical aperture.

The most accurate determinations of FISH spot counts in cells on flat substrates are currently based on high-resolution fluorescence images taken at different focal planes across the depth of the cell. The resulting set of two-dimensional (2D) images are reconstructed into a three-dimensional (3D) representation of the cell, and FISH spots are counted both within and across the image planes to ensure that superimposed FISH spots within a single image are resolved across the multiple images. While such image stacking techniques can effectively resolve superimposed FISH spots, existing systems for 3D cell imaging are slow, often requiring several minutes to create each 3D composite. As a result, the various 2D images are gathered at widely different times, and changes in the cell over the course of the imaging process alter the resulting 3D representation. Further, such systems cannot tolerate movement of the cells during the imaging process, which limits their application to fixed cells that are immobilized on slides. An improved system would allow the rapid 3D imaging of cells, including cells in motion.

Accordingly, it will be apparent that an improved technique is desired that resolves the limitations in analyzing the three-dimensional features of both stationary and moving cells imposed by the conventional approaches discussed above. In addition, a new approach developed to address these problems in the prior art should also have application to the analysis of other types of objects besides cells and should be amenable to implementation in different configurations to meet the specific requirements of disparate applications of this technology.

SUMMARY OF THE INVENTION

The present invention is directed to an imaging method and system that is adapted to determine one or more characteristics of an object from an image of the object. There can be relative movement between the object and the imaging system, and although it is contemplated that either (or both) may be in motion, the object will preferably move while the imaging system is fixed in position. In addition, it should also be understood that while much of the following disclosure recites "an object," it is likely that the present invention will preferably be used with a plurality of objects and is particularly useful in connection with imaging a stream of objects or objects moving within a substrate, e.g., in narrow capillaries. Also, it should be understood that as used herein and in the following claims, the terms "image" and "imaging" are broadly applied and are intended to generally refer to the light from an object or objects that is directed onto a surface of a detector; thus, these terms are intended to encompass light from an object or objects that is diffused, dispersed, or blurred on the surface of a detector, as well as light from an object or objects that is focussed onto the surface of the detector, and light from an object or objects that is divided into one or more spectral components incident on the surface of the detector.

The present invention may be applied to the rapid analysis of cells in three dimensions for purposes such as biological warfare agent detection, prenatal diagnosis, cancer screening, drug discovery, and other applications. To achieve such functional capabilities, the present invention collects image data from multiple focal positions within moving or stationary cells. Further, these data may be acquired over a large spectral range with high spectral and spatial resolution. The present invention preserves the spatial origin of the spectral information gathered from the object, enabling the discrimination of small sources of the same or different colored light emanating from the object. To accomplish these tasks, the present invention employs novel combinations of Time-Delay-Integration (TDI) imaging, synchronous and non-synchronous signal generation, and uses an optical system with an inclined detector orientation, and in some cases, a spectral dispersing element.

The TDI detector that is used in the various embodiments of the present invention preferably comprises a rectangular charge-coupled device (CCD) that employs various specialized pixel read out algorithms. Standard, non-TDI CCD arrays are commonly used for 2D imaging in cameras. In a standard CCD array, photons that are incident on a light sensitive element (corresponding to one pixel of an image and therefore referred to herein as a "pixel") produce charges that are trapped in the element. After image acquisition, the photon charges from each light sensitive pixel are read into an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In a TDI detector comprising a CCD array of physical pixels, the CCD array remains exposed to the light as the pixels are read out. The projection of an image on the array of physical pixels generates a pixilated signal. The readout typically occurs one row at a time, e.g., from the top to the bottom of the array. Once a first row is read out, the signal pixels in the remaining rows are shifted by one physical pixel in the direction of the row that has just been read. If the object being imaged onto the array moves in synchrony with the motion of the signal pixels, light from the object is integrated without image blurring for the duration of the TDI detector's total readout period. The signal strength produced by a TDI detector increases linearly with the integration period, which is proportional to the number of physical TDI pixel rows, but the noise increases only as the square root of the integration period, resulting in an overall increase in the signal-to-noise ratio (SNR) compared to a conventional CCD array, by a factor equal to the square root of the number of rows.

In the present invention, there are four entities that may be in motion. These include the object being imaged, the image of the object projected on the detector, the detector itself, and the pixilated signal generated by the image on the detector. Any relative movement between the object and the detector results in movement of the image across the detector. TDI imaging, unlike other imaging methods, involves the movement of the pixilated signal across the detector while the measurement is being performed. In many cases, it is contemplated that the image of the object will move across the detector. However, the pixilated signal may not move in synchrony with the image of the object. In the present invention, the velocity of signal motion is a controllable parameter that can be adjusted in order to measure various features of the object being imaged. The signal can be made to move faster, slower, or in a different direction than the image, which may or may not itself be moving. Further, the movement of the signal can be changed dynamically during the measurement. The nature of the asynchrony in part determines the features of an object or objects that can be measured.

In TDI imaging of objects that was disclosed in previous pending applications, the image of the object moves synchronously with the pixilated signal (in the same direction and with the same speed), light forming each portion of the image is collected in the same portion of the pixilated signal over time, regardless of the motion. Conversely, if the image of the object moves asynchronously relative to the pixilated signal, (at a different speed and/or in a different direction), light forming each portion of the image at later times will not be collected in the same portion of the pixilated signal. By intentionally desynchronizing the motion of the pixilated signal on the TDI detector from the motion of the image, temporally distinct pixilated signals are produced. In the present invention, this effect, coupled with an inclination of the detector relative to the plane formed by the motion of the objects, can produce distinct images from different focal positions within the object. In the present invention, when the pixilated signal moves synchronously with the image, a characteristic signal intensity profile is produced that can be used to identify point sources of light such as those created by FISH probes.

Another adjustable parameter in the present invention is the continuity of signal generation. In some embodiments of the invention, the signal from the object is detected continuously. An exemplary application of continuous detection would be the imaging of a cell containing a chemiluminescent substrate that constantly emits light. Another example would be a cell illuminated by a continuous-wave laser or arc lamp to form a scatter, absorption, or fluorescence image on the detector. In other embodiments of the invention, the signal from the object is detected in a discontinuous fashion. For example, discontinuous detection would occur if a cell is illuminated by a pulsed or modulated laser to form transient scatter, absorption, or fluorescence images on the detector. Another example of discontinuous detection would be if a chemiluminescent cell is imaged via a shuttered or gated TDI detector. Signal continuity, when controlled in combination with the orientation of the detector plane and the synchrony of signal readout, gives rise to numerous embodiments and modes of operation of the present invention.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIGS. 1A, 1B, and 1C respectively show a plan view, an elevational view, and an isometric view of an exemplary imaging system suitable for implementing the present invention, in which particles conveyed by a fluid stream are imaged on a TDI detector;

FIGS. 3A and 3B are views over time illustrating the operation of a first embodiment in which an object is detected continuously, and signals produced from images of the object are clocked synchronously to produce a composite image containing information from a plurality of different focal planes across a depth of the object;

FIG. 3C illustrates the characteristic intensity profile of a luminescent point source imaged by the first embodiment;

FIGS. 4A–4F are a plurality of images of an object over time, illustrating discontinuous imaging wherein the pixilated detector signals are clocked more rapidly than image movement over the TDI detector;

FIGS. 5A–5F are a plurality of images of an object over time, illustrating discontinuous imaging wherein the pixilated detector signals are clocked more slowly than image movement over the TDI detector;

DESCRIPTION OF THE PREFERRED EMBODIMENT

Figure 1A:
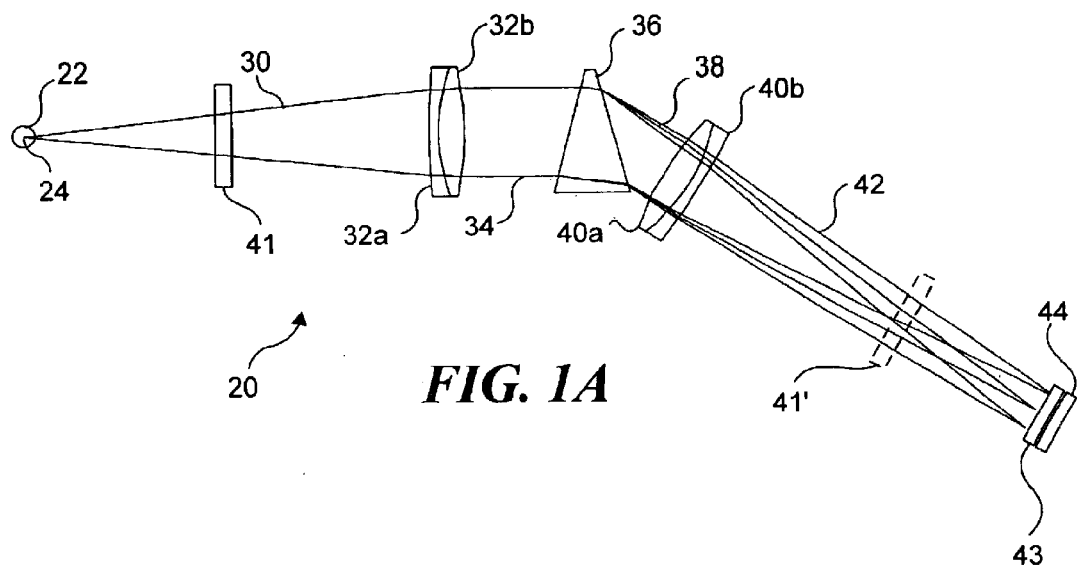

The present invention offers considerable advantages over systems employed for cell and particle analysis in the prior art. These advantages arise from the use in the present invention of an optical dispersion system in combination with a TDI detector to produce an output signal in response to the images of cells and other objects that are directed on the TDI detector. Multiple objects can be imaged on the TDI detector at the same time. In addition, the image of each object can be spectrally decomposed to discriminate object features by absorption, scatter, reflection, or probe emissions using a readily available TDI detector for the analysis.

The present invention can be employed to determine morphological, photometric and spectral characteristics of cells and other objects by measuring optical signals including light scatter, reflection, absorption, fluorescence, phosphorescence, luminescence, etc. Morphological parameters include nuclear area, perimeter, texture or spatial frequency content, centroid position, shape (i.e., round, elliptical, barbell-shaped, etc.), volume, and ratios of any of these parameters. Similar parameters can also be determined for the cytoplasm of cells with the present invention. Photometric measurements with the invention enable the determination of nuclear optical density, cytoplasm optical density, background optical density, and the ratios of any of these values. An object being imaged with the present invention can be stimulated into either fluorescence or phosphorescence to emit light, or may be luminescent, producing light without stimulation. In each case, the light from the object is imaged on the TDI detector of the present invention, and the output signal of the TDI detector analyzed to determine the presence and amplitude of the emitted light, the number of discrete positions in a cell or other object from which the light signal(s) originate(s), the relative position of the signal sources, and the color (wavelength or waveband) of the light emitted at each position in the object.

An initial application of the imaging system comprising the present invention will likely be as a cell analyzer to determine one or more of the parameters listed above, for cells entrained in a fluid flowing through the imaging system. However, it should also be understood that this invention can be used for imaging other kinds of moving objects.

The present invention concerns alternative detector configurations and modes of operation in connection with various imaging system embodiments disclosed in commonly assigned copending patent applications, including Ser. Nos. 09/490,478 and 09/538,604, the specification and drawings of which are hereby specifically incorporated herein by reference. For convenience, portions of the first of the above-noted applications are reproduced below in order to facilitate access to portions of its disclosure that will enable a reader to better understand how various embodiments of the present invention are implemented. However, it will be understood that the present invention can be implemented with other imaging system configurations disclosed in the above-referenced applications, which are not specifically discussed herein, as well as other imaging systems of related configuration.

Figure 1B:
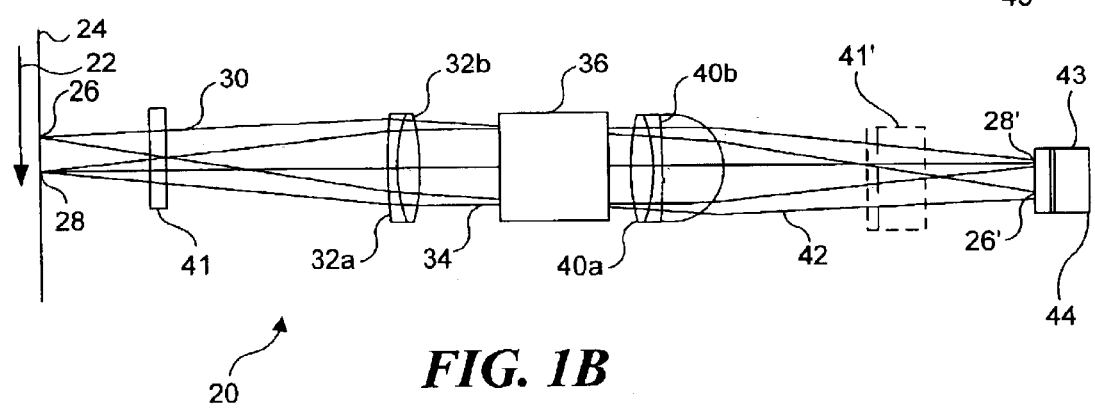
Figure 1C:
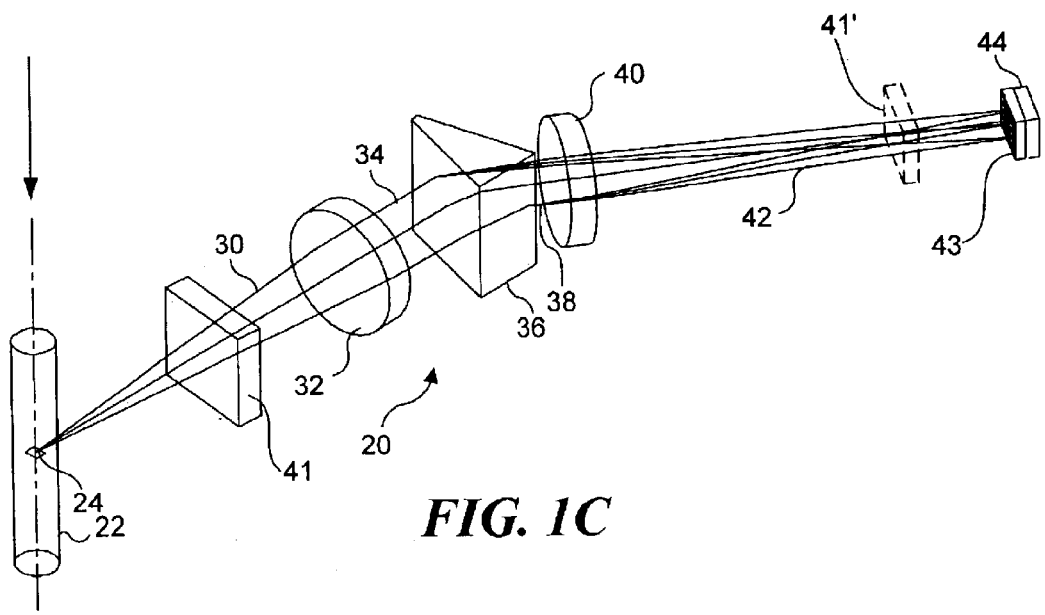

A first exemplary configuration of an imaging system 20 that is suitable for implementation of the preferred embodiments of the present invention described below is schematically illustrated in FIGS. 1A–1C, in connection with producing images of moving objects such as cells that are conveyed by a fluid flow 22 through the imaging system. In FIG. 1A, fluid flow 22 entrains an object 24 (such as a cell, but alternatively, a small particle of a different sort) and carries the object through the imaging system. The direction of the fluid flow in FIG. 1A is into (or out of) the sheet, while in FIGS. 1B–1C, the direction of fluid flow is from top to bottom, as indicated by the arrow to the left of the Figures. Light 30 from object 24 passes through collection lenses 32a and 32b that collect the light, producing collected light 34, which is approximately focussed at infinity, i.e., the rays of collected light are generally parallel. Collected light 34 enters a dispersing element 36, which disperses the light, producing dispersed light 38. The dispersed light then enters imaging lenses 40a and 40b, which focusses light 42 onto a TDI detector 44. It should be noted that as used throughout this document, a TDI detector can generally be oriented in different positions, so that the terms "row" and "column," "up" and "down," and "left" and "right" as applied to a TDI detector are only meaningful in regard to each exemplary illustration, but are not intended to be limiting in regard to the scope of the claims.

As shown in the Figures, imaging system 20 may optionally include a shutter 41 or a gated image intensifier 43. In these instances, Shutter 41 or gated image intensifier 43 are used to interrupt the light directed onto the TDI detector and thus interrupt the formation of images produced by the system of the detector, so as to produce a discontinuous image that falls upon TDI detector 44. In general, shutter 41 can be placed anywhere along the light path, including between object 24 and the collection lenses 32a and 32b, or between imaging lenses 40a and 40b and TDI detector 44. An exemplary alternative disposition is indicated in the Figure by a shutter 41'. Preferably, gated image intensifier 43 will be disposed between the imaging lenses and the TDI detector, although this exemplary disposition is not limiting, as will be understood by those skilled in the optical arts. Further details of the use of shutter 41 and gated image intensifier 43 in the present invention are discussed below.

With reference to FIG. 1B, if it is assumed that the Figure depicts the imaging of object 24 over time, the object is shown at both a position 26 and a position 28 as it moves with fluid flow 22. As a consequence, images of object 24 will be produced on the detector at two discrete spatial positions 26' and 28', as indicated on the right side of FIG. 1B. Alternatively, if it is assumed that FIG. 1B is depicting a single instant in time, positions 26 and 28 represent the location of two separate objects, which are simultaneously imaged on the detector at positions 26' and 28'.

In regard to imaging system 20 and all other imaging systems illustrated herein, it will be understood that the lenses and other optical elements illustrated are shown only in a relatively simple form. Thus, the collection lens is illustrated as a compound lens comprising only collection lenses 32a and 32b. Lens elements of different designs, either simpler or more complex, can alternatively be used in constructing the imaging system to provide the desired optical performance, as will be understood by those of ordinary skill in the art. The simplicity or complexity of the actual lenses or optical elements used in the imaging system will depend upon the particular type of imaging application for which the imaging system will be employed. It is further noted that imaging systems not including a light-dispersing element such as prism 36, may also be implemented to provide the present invention.

It will be understood that relative movement exists between the object being imaged and the imaging system. In most cases, it will be more convenient to move the object than to move the imaging system. However, it is also contemplated that in some cases, the object may remain stationary and the imaging system, move relative to it. As a further alternative, both the imaging system and the object may be in motion, but either in different directions or at different rates.

The TDI detector that is used in the various embodiments of the present invention preferably comprises a rectangular charge-coupled device (CCD) that employs a specialized pixel read out algorithm, as explained below. Non-TDI CCD arrays are commonly used for 2D imaging in cameras. In a standard CCD array, photons that are incident on a pixel produce charges that are trapped in the pixel. The photon charges from each pixel are read out of the detector array by shifting the charges from one pixel to the next, and then transferring the charges to an output capacitor, producing a voltage proportional to the charge. Between pixel readings, the capacitor is discharged and the process is repeated for successive pixels on the chip. During the readout, the array must be shielded from any light exposure to prevent charge generation in the pixels that have not yet been read.

In one type of TDI detector 44, which comprises a CCD array, the CCD array remains exposed to the light as the pixels are read out. The readout occurs one row at a time from the top toward the bottom of the array. Once a first row is read out, the remaining rows are shifted by one pixel in the direction of (i.e., toward) the row that has just been read. If the object being imaged onto the array moves in synchrony with the motion of the pixels, light from the object is integrated for the duration of the TDI detector's total readout period without image blurring. The signal strength produced by a TDI detector increases linearly with the integration period, which is proportional to the number of TDI rows, but the noise increases only as the square root of the integration period, resulting in an overall increase in the SNR by a factor equal to the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have a different configuration of rows and columns or a nonrectilinear arrangement of pixels. The Dalsa sensor has approximately 96 times the sensitivity and nearly 10 times the SNR of a conventional CCD array. The extended integration time associated with TDI detection also serves to average out temporal and spatial illumination variations, increasing measurement consistency.

In imaging system 20 and in other exemplary imaging systems described herein that employ a fluid flow to carry objects through the imaging system, a flow-through cuvette or a microcapillary (not shown) contains the cells or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector can be selectively controlled, as required, to match the motion of the sample solution.

Various optical magnifications can be used to achieve a desired resolution of the object that is being imaged on the light sensitive regions (pixels) of the TDI detector. It is contemplated that in most embodiments, the optical magnification will fall within a range of 1:1 to 50:1, providing a substantial range in the number of light sensitive regions on the TDI detector on which images of the object are formed. The number of regions will also depend on the actual size of the object being imaged and its distance from the imaging system. It is envisioned that the present invention has applications to technology ranging from the analysis of cells and other microscopic objects to the imaging of stellar objects.

It should be emphasized that the present invention is not limited to CCD types of TDI detectors. Other types of TDI detectors, such as complementary metal oxide semiconductor (CMOS) and multi-channel plate imaging devices might alternatively be used for the TDI detector in the present invention. It is important to understand that any pixilated device (i.e., a device having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired effect.

First Preferred Embodiment

Figure 2:
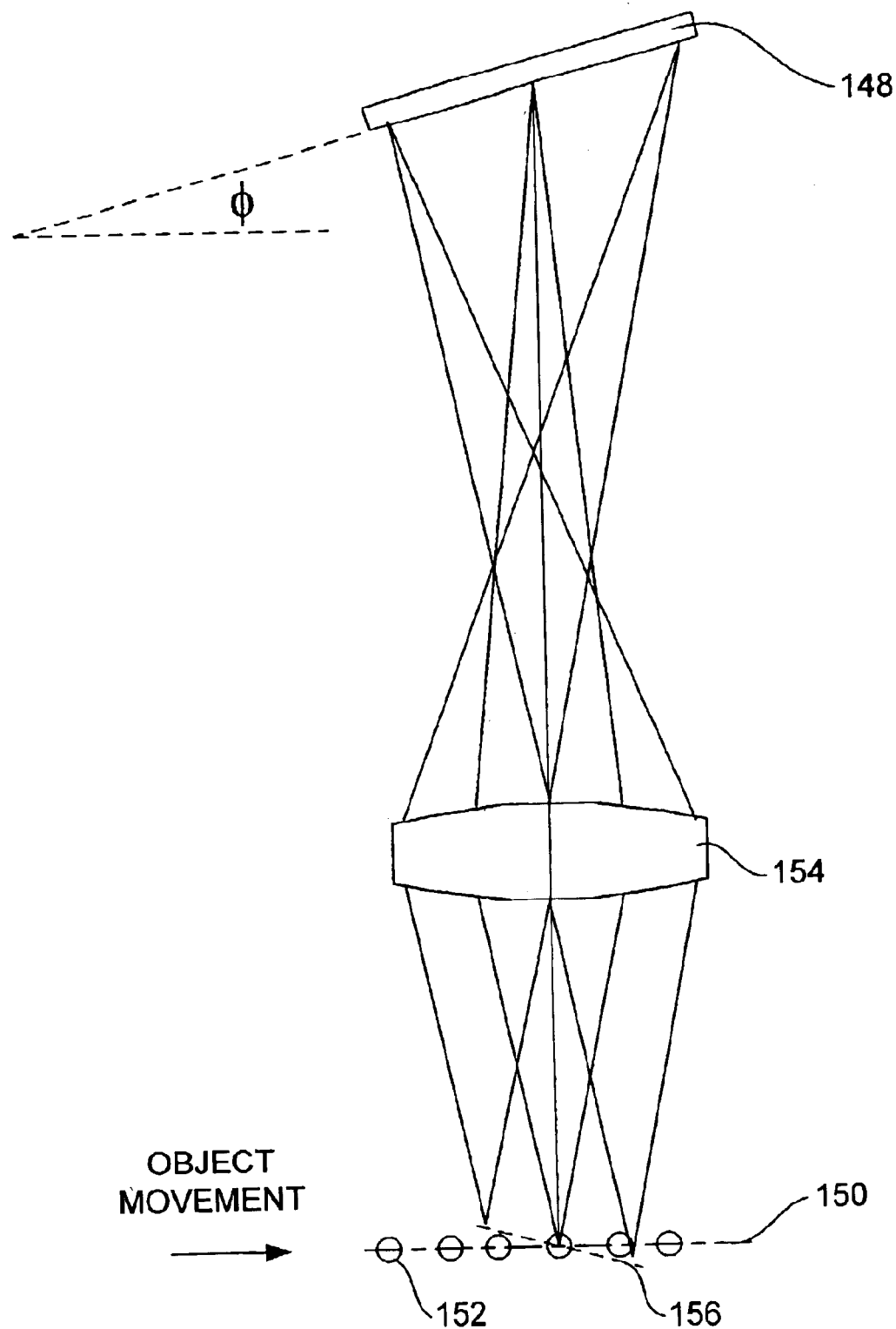
FIG. 2 illustrates the focal positioning effects of tilting the TDI detector plane in an optical system relative to the plane defined by the motion of the objects traversing the field of view.

In accord with a first preferred embodiment, TDI clocking is synchronous with the motion of the image of the object, the signal is detected continuously, and the TDI detector is oriented in a plane inclined relative to the axis of motion of the object. Such a configuration is shown in FIG. 2 and it includes a TDI detector 148 that is tilted at an incline angle $\phi$ relative to an object motion axis 150. An object 152 is traveling along object motion axis 150 and is imaged on TDI detector 148 by an imaging lens 154. The inclination of the detector plane produces an inclined plane of focus 156, as illustrated in the Figure. In this configuration, measurements taken at different times will have different planes of focus within the object. However, because the first preferred embodiment employs synchronous clocking and continuous detection, only a single image is formed. Synchronous clocking with an inclined detector requires a different clocking frequency than when the detector is parallel to the axis of motion. For a given angle $\phi$ between the detector plane and the axis of motion, the projected velocity of the detector signal $V_s$ in the axis of object motion is $$V_s' = V_s * \mathrm{Cos}(\phi). \tag{1}$$

The inclined detector therefore requires a slightly higher TDI clock rate to maintain synchronous operation.

In this first preferred embodiment of the present invention, the TDI detector operates in synchronous mode, with continuous signal detection. In this embodiment, the TDI detector output signal is continuously monitored during the entire traversal period of the image across the TDI detector. The inclination of the TDI detector causes the plane of focus of the imaging optics to sweep the image of the object across the TDI detector, continuously superimposing image signals on the TDI detector. However, because the TDI detector is operated in synchronous mode, there is no lateral shift between the superimposed image signals. The net effect is equivalent to "racking focus" through an object while collecting image signals.

This focus racking effect can be used to enhance the detection of luminous point sources such as FISH probes within a cell. FISH signals can originate anywhere within a cell nucleus, which is typically 10 microns in diameter. Because the depth of focus of a typical cell imaging system is less than one micron, FISH signals can be located well outside of the plane of focus of a single image. The first preferred embodiment enables the simplified detection of such signals via the analysis of a single composite image from a system employing continuous detection.

Luminous point sources that lie outside of the plane of focus produce wide illumination regions with intensity profiles that are not steeply inclined, making them difficult to detect and enumerate. By racking focus through the cell, every FISH signal within that cell will pass through the plane of focus and take on a peaked intensity profile in the resulting image, regardless of the original position of the FISH probes in the cell. This point is illustrated by FIGS. 3A, 3B, and 3C. FIG. 3A shows the position of a FISH spot 170 (produced by imaging a FISH probe within a cell 58) relative to an inclined focal plane 172 over time, drawn from a perspective orthogonal to the optic axis of the imaging system. FIG. 3B is a view of TDI detector 148 from a perspective along the optic axis of the imaging system. When inclined focal plane 170 enters cell 58, TDI detector 148 detects a blurred image 174 of FISH spot 170. As FISH spot 170 moves closer to inclined focal plane 172, the FISH spot's corresponding image 174 on TDI detector 148 becomes less blurred. Because the image is continuously detected in synchronization with the moving cell, image 174 will reflect a gradient change in size and intensity of FISH spot 170 within image 174. However, for clarity, each image 174 is shown at discrete times, $t_1$ through $t_5$, with discrete sizes and discrete intensity levels. The image size reaches a minimum when FISH spot 170 passes through inclined focal plane 172 (i.e., at time $t_3$). Thereafter, FISH spot 170 recedes from the focal plane, spreading its image over an increasingly larger area of TDI detector 148.

FIG. 3C illustrates the characteristic inverse square intensity profile of a composite image produced by this preferred embodiment. Since the signal produced by image 174 is spread over a smaller area as FISH spot 170 approaches inclined focal plane 172, the intensity profile of the signal becomes steeper and achieves a maximum slope upon intersection with the focal plane. The high, sharp peak of the profile is more easily recognized by threshold algorithms, while the characteristic inverse squared slope of the profile can be used as a signature to distinguish FISH probe signals from image artifacts or noise.

Second Preferred Embodiment

Like the first preferred embodiment, the second preferred embodiment employs a TDI detector inclined at an angle $\phi$ relative to the apparent axis of motion of the object. However, unlike the first embodiment, in the second preferred embodiment, signal detection is discontinuous. Discontinuous detection can occur as a result of employing a pulsed laser or other type of pulsed or strobed light source to illuminate the object. If the object being imaged is chemiluminescent or if the light from the object is continuous for some other reason, such as the object being illuminated by a continuous light source, a shutter or gated image intensifier can be employed between the object and the detector to produce discontinuous detection, such as described above with reference to shutter 41 and gated image intensifier 43 in FIGS. 1A–1C.

Also, unlike in the first preferred embodiment, a signal readout from the TDI detector in the second preferred embodiment is asynchronous, such that the velocity of the pixilated signal differs from the velocity of the image for at least part of the time that the image of the object is projected on the TDI detector. The difference between the signal and image velocities causes a divergence over time between the position of the image and the detector signal. There are three modes of asynchronous operation of the second embodiment. In the first mode of operation, the pixilated signal is clocked across the TDI detector more rapidly than the movement of the image. In the second mode of operation, the pixilated signal is clocked across the TDI detector more slowly than the movement of the image. And, in the third mode of operation, the TDI detector operates quasi-synchronously with the movement of the image. In quasi-synchronous operation, the pixilated signal is clocked synchronously with the image to extend the signal integration time, followed by a period of asynchronous clocking, employed to separate the image from the pixilated signal on the detector.

In the simplest case of a TDI detector with no inclination relative to the axis of motion, the time $T_p$ required for the image and the signal to diverge by one row of pixels is defined by:

$$T_p = |P/(V_s - V_i)|. \qquad (2)$$

where the velocity of the image across the detector is $V_i$, the velocity of the TDI detector signal is $V_s$, and the pixel height is P. Note that the two velocities can be in opposite directions. In the case of the inclined detector, the velocity of the detector signal $V_s$ is replaced with the projected velocity $V_s'$ of Equation (1) such that:

$$T_p = |P/((V_s * \cos(\phi)) - V_i)|. \qquad (3)$$

The divergence of the signal and image on the TDI detector during asynchronous operation enables the second preferred embodiment to gather independent images of a single object over time. The time resolution of the system is governed by Equation (3), as well as being a function of the image height. When the image of an object is N pixels high on the TDI detector, the time required to prevent the overlap of two successive images is:

$$T_p = (N*P)/((V_s*\cos(\phi)) - V_i) \qquad (4)$$

In this mode of operating the second preferred embodiment, discontinuous detection is used to increase image acquisition throughput and to prevent image blurring, despite the difference between signal and image velocities produced by asynchronous readout of the TDI detector. Image integrity is preserved by limiting the object's detection time to less than $T_p$, the time required for the image and the signal to diverge on the TDI detector by one pixel. Preferably, control of the detection period is achieved by controlling the duration of illumination. In the case of objects that continuously emit light, the TDI detector is shuttered and is exposed to light from the object for a time less than $T_p$. After a detection period, a subsequent detection period is delayed until the image and the signal have diverged on the detector by a distance equal to or greater than the image height. In this manner, multiple unblurred images of an object can be detected in rapid succession. In comparison to a frame-mode detector, which must be completely read out after each detection period, the second embodiment can produce higher image acquisition rates by a factor approximately equal to the ratio of the detector height to the image height.

FIGS. 4A–4F include a plurality of time frames corresponding to a time-series illustration of the first operating mode of the second preferred embodiment. In a first time frame 64, illumination 62 of cell 58 is limited to less than the time it takes a first image 76 to travel one pixel on TDI detector 44, halting before a second time frame 66. In second time frame 66, a first signal 78 generated by the first image is clocked down TDI detector 44 at a velocity ratio of four pixels of signal movement on the TDI detector for each pixel of image movement. In a third time frame 68, first signal 78 has diverged from the position of cell 58 on TDI detector 44, and illumination 62 is restored briefly to generate a second image 80. Illumination is again halted by a fourth frame 70, while first signal 78 and a second signal 82 produced in response to second image 80 propagate down the detector until the divergence has again exceeded the image height. This process continues, generating numerous image signals at different times for a cell that is in view, as shown by a third image 84 and a third signal 86 in FIGS. 4E and 4F, corresponding to fifth and sixth time frames 72 and 74.

With reference to FIGS. 5A–5F, a plurality of time frames 88, 90, 92, 94, 96, and 98 produced in accord with the second operating mode of the second embodiment are shown. In this mode, the velocity of cell 58 is higher than the clock rate of the signals from TDI detector 44, in contrast to FIGS. 4A–4F, wherein the clock rate of the signals is higher than the velocity of the cell. Images 76, 80, and 84 are incident of the TDI detector, producing corresponding signals 78, 82, and 86. Otherwise, operation of the system is comparable to that described above with reference to FIGS. 4A–4F. The third mode of operation for the second preferred embodiment is not illustrated.

Figures 6A, 6B:
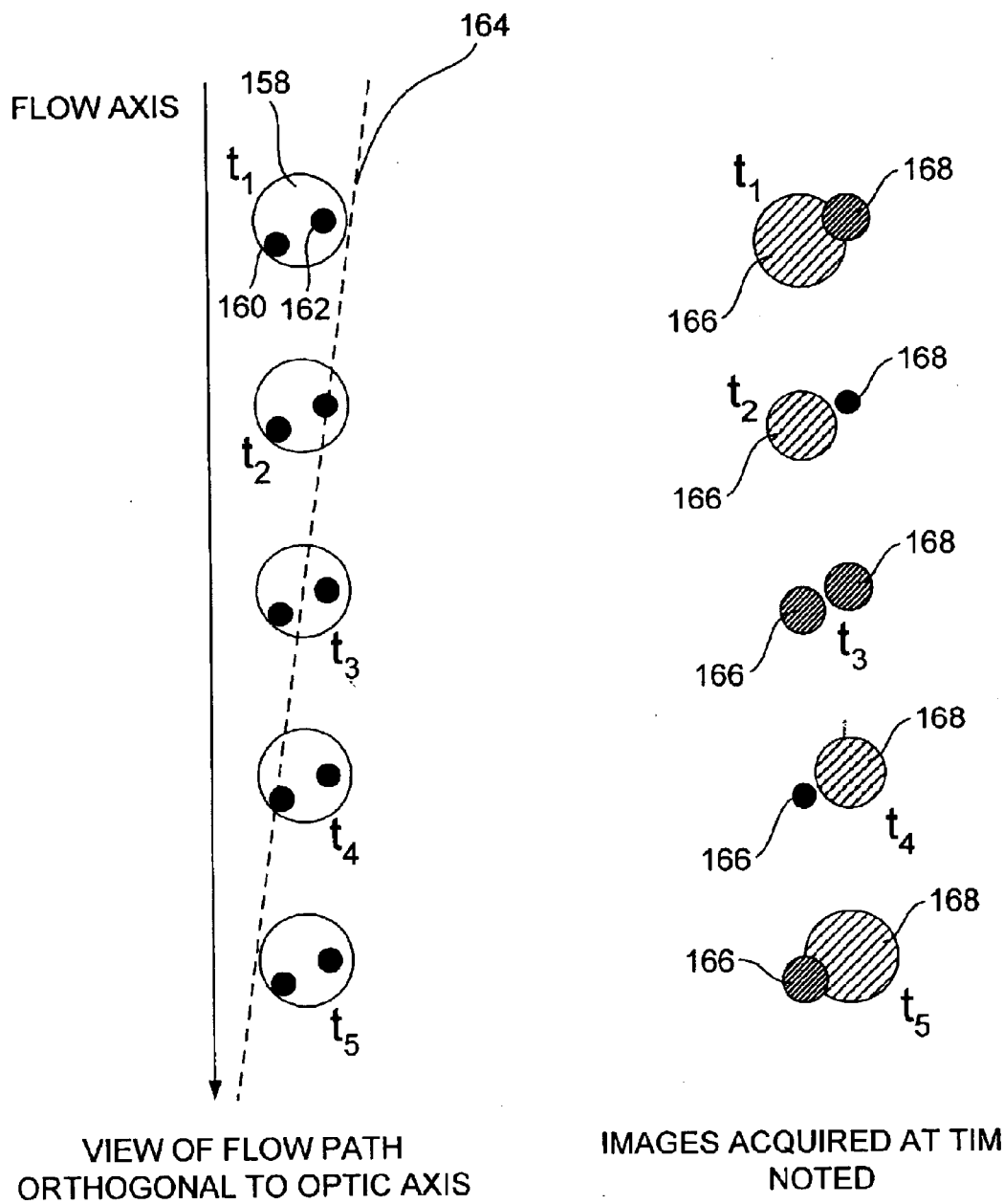
FIG. 6A is a view over time illustrating the position of two luminescent point sources located at different depths within a cell with respect to the TDI detector plane.
FIG. 6B illustrates characteristic images of two luminescent point sources located at different depths within a cell being imaged by a second embodiment.

The inclination of the detector in the second preferred embodiment causes each discrete image to lie at a different focal plane within the object. The 2D images measured at different focal planes across the object can then be reconstructed into a 3D representation of the object. FIGS. 6A and 6B illustrate this aspect of the second preferred embodiment. FIG. 6A is a view of the flow path of a cell nucleus 158 over time, looking in a direction orthogonal to the optic axis of the imaging system. Cell nucleus 158 contains two FISH probes 160 and 162 disposed at different distances from an inclined focal plane 164 at different times. FIG. 6B is a view of TDI detector 148 looking along the optic axis of the imaging system. FIG. 6B shows images 166 and 168 of FISH probes 160 and 162, respectively, taken at various positions of cell nucleus 158 relative to inclined focal plane 164, which is shown in FIG. 6A. Images 166 and 168 exemplify the image spreading incurred when a feature of interest, such as FISH probes 160 and 162, is out of focus when imaged on the detector. Since cell nucleus 158 is a 3D object, FISH probes 160 and 162, which are contained with the cell nucleus, are unlikely to be in focus simultaneously. The use of the inclined TDI detector enables images to be gathered at different focal planes within cell nucleus 158, so that the 3D spatial relationship between the FISH probes can be resolved.

From the above discussion, it will be clear to those skilled in the art that the concept of inclining a TDI detector to detect signals at different planes of focus can be applied to any of the disclosed preferred embodiments of the present invention that were included in the above-referenced patent applications, and is not limited to the embodiments discussed hereinabove. Accordingly, the invention is broadly applicable to many applications in which a TDI detector is used for imaging objects.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A system for obtaining at least one output signal corresponding to at least one image of an object-wherein there is relative motion between the object and the system, comprising:
   (a) a collection lens disposed so that light traveling from the object passes through the collection lens and travels along a collection path, said collection lens substantially collimating light from the object;
   (b) an imaging lens disposed in the collection path to receive light that has passed through the collection lens, producing focused light that is directed along an imaging path; and
   (c) a time delay integration (TDI) detector configured to generated at least one output signal corresponding to at least one image of the object, said TDI detector disposed to receive the focused light directed along the imaging path, said TDI detector being inclined at an angle relative to the imaging path, so that a plane of the TDI detector is not perpendicular to the imaging path, and so that light from the imaging path that is incident on a first part of said TDI detector forms an image exhibiting a first focus, while light from the imaging path that is incident on a different part of said TDI detector forms an image exhibiting a different relative focus.

2. An imaging system configured to produce at least one image of an object while there is relative movement between the object and the imaging system, comprising:
   (a) a collection lens disposed so that light traveling from the object passes through the collection lens and travels along a collection path, said collection lens substantially collimating light from the object;
   (b) a focusing lens disposed in the collection path to receive light that has passed through the collection lens, producing focused light that is directed along an image path; and
   (c) a light sensitive detector disposed to receive the focused light directed along the image path, said detector being disposed at an angle relative to the focusing lens, such that light from the image path that is incident on a first part of said detector exhibits a first focus, while light from the image path that is incident on a different part of said detector exhibits a different focus.

3. The system of claim 1, wherein the at least one output signal propagates over the TDI detector with a velocity that is substantially asynchronous with that of a corresponding image of the object formed on the TDI detector.

4. An imaging system for obtaining at least one output signal corresponding to at least one image of an object wherein there is relative motion between the object and the system, comprising:
   (a) an imaging lens disposed to focus light from the object and direct the focused light along an imaging path; and
   (b) a time delay integration (TDI) detector configured to generated at least one output signal corresponding to at least one image of the object, said TDI detector disposed to receive the focused light directed along the imaging path and being inclined at an angle relative to the imaging lens, so that a plane of the TDI detector is not parallel to a longitudinal axis of the imaging lens, such that light from the imaging lens that is incident on a first part of said TDI detector forms a first image, while light from the imaging lens that is incident on a second part of said TDI detector forms a second image, the first image and the second image being characterized by exhibiting a different relative focus.

5. The imaging system of claim 4, wherein the at least one output signal propagates over the TDI detector with a velocity that is substantially asynchronous with that of a corresponding image of the object formed on the TDI detector.

6. The imaging system of claim 4, further comprising a collection lens disposed so that light traveling from the object passes through the collection lens and travels along a collection path, said collection lens substantially collimating light from the object, the imaging lens being disposed in the collection path.

7. An imaging system configured to produce at least one image of an object while there is relative movement between the object and the imaging system, comprising:

(a) an imaging lens disposed to direct light from the object along an image path; and (b) a light sensitive detector disposed to receive the light from the object directed along the image path, said detector being disposed at an angle relative to the imaging lens, such that light from the image path that is incident on a first part of said detector forms a first image, while light from the image path that is incident on a different part of said detector forms a different image, the first image and the different image exhibiting a different relative focus, such that if the first image is in focus, the different image is not in focus, and if the different image is in focus, the first image is not in focus.

8. The imaging system of claim 7, further comprising a collection lens disposed so that light traveling from the object passes through the collection lens and travels along a collection path, said collection lens substantially collimating light from the object, the imaging lens being disposed in the collection path.

9. The imaging system of claim 7, wherein the light sensitive detector comprises a time delay integration (TDI) detector producing at least one output signal corresponding to at least one image of the object.

10. The imaging system of claim 9, wherein the at least one output signal propagates over the TDI detector with a velocity that is substantially asynchronous with that of a corresponding image of the object formed on the TDI detector.

* * * * *